(12) United States Patent
Kovi et al.

(10) Patent No.: US 11,324,771 B2
(45) Date of Patent: May 10, 2022

(54) PROCESS FOR THE PREPARATION OF HYDROXOCOBALAMIN HYDROCHLORIDE

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Shivnath Patil, Dhule (IN); Chowdari Bhushaiah Talluri, Dayton, NJ (US); Aditya Khanvilkar, Vadodara (IN); Govind Ahirrao, Jalgaon (IN)

(73) Assignee: RK Pharma Solutions LLC, Piscataway, NJ (US)

( * ) Notice: Subject to any disclaimer, the term of this patent is extended or adjusted under 35 U.S.C. 154(b) by 0 days.

(21) Appl. No.: 16/910,560

(22) Filed: Jun. 24, 2020

(65) Prior Publication Data
US 2021/0252037 A1 Aug. 19, 2021

(30) Foreign Application Priority Data

Feb. 12, 2020 (IN) .............................. 202021006047

(51) Int. Cl.
| | | |
|---|---|---|
| *C07H 1/06* | (2006.01) | |
| *C07H 23/00* | (2006.01) | |
| *A61K 31/714* | (2006.01) | |

(52) U.S. Cl.
CPC .............. *A61K 31/714* (2013.01); *C07H 1/06* (2013.01); *C07H 23/00* (2013.01)

(58) Field of Classification Search
CPC ......... A61K 31/714; C07H 1/06; C07H 23/00
See application file for complete search history.

(56) References Cited

U.S. PATENT DOCUMENTS

| | | |
|---|---|---|
| 3,138,583 A | 6/1964 | Boige et al. |
| 3,167,539 A | 1/1965 | Smith |
| 3,448,099 A | 6/1969 | Boige |
| 5,338,418 A | 8/1994 | Hirayama et al. |

FOREIGN PATENT DOCUMENTS

| | | | |
|---|---|---|---|
| CN | 102351933 A | * | 2/2012 |
| CN | 110146612 A | * | 5/2019 |
| GB | 1012360 A | | 12/1965 |
| WO | 2014/142640 A1 | | 9/2014 |

OTHER PUBLICATIONS

Casazza Bruno, U. et al., machine translation of WO 2014/142640 A1, published Sep. 2014, 25 pages (Year: 2014).*
Wang et al., machine translation of CN 102351933A, published Feb. 2012, 7 pages (Year: 2012).*
Liu Junqi et al., machine translation of CN 110146612, published Aug. 2019, 10 pages (Year: 2019).*

* cited by examiner

*Primary Examiner* — Bahar Craigo
(74) *Attorney, Agent, or Firm* — Antonio Papageorgiou; Lombard & Geliebter LLP

(57) ABSTRACT

A process for the preparation of hydroxocobalamin hydrochloride. More particularly the present application relates to improved process for the preparation of Hydroxocobalamin hydrochloride. In addition the present application also relates to process for the preparation of novel amorphous form. This application particularly relates to a process for the industrial manufacture of hydroxocobalamin hydrochloride from cyanocobalamin. The present application also relates to the improvement in yield with better purity of Hydroxocobalamin hydrochloride.

6 Claims, 6 Drawing Sheets

PROCESS FOR THE PREPARATION OF HYDROXOCOBALAMIN HYDROCHLORIDE

FIELD OF THE INVENTION

The present application relates to Hydroxocobalamin of formula I. Specifically, the present application relates to improved process for the preparation of Hydroxocobalamin hydrochloride of formula II. In addition, the present application also relates to process for the preparation of novel amorphous form.

This application particularly relates to a process for the industrial manufacture of hydroxocobalamin hydrochloride from cyanocobalamin. The present application also relates to the improvement in yield with better purity of Hydroxocobalamin hydrochloride.

BACKGROUND OF THE INVENTION

Hydroxocobalamin (also called Cyanokit®) is cobinamide dihydroxide dihydrogen phosphate (ester), mono (inner salt), 3'-ester with 5,6-dimethyl-1-α-D-ribofuranosyl-1H-benzimidazole. The drug substance is the hydroxylated active form of vitamin B12 and is a large molecule in which a trivalent cobalt ion is coordinated in four positions by a tetrapyrol (or corrin) ring. It is a hygroscopic, odorless, dark red, crystalline powder that is freely soluble in water and ethanol, and practically insoluble in acetone and diethyl ether. Hydroxocobalamin has a molecular weight of 1346.36 atomic mass units, an empirical formula of $C_{62}H_{89}CoN_{13}O_{15}P$ and the following structural formula:

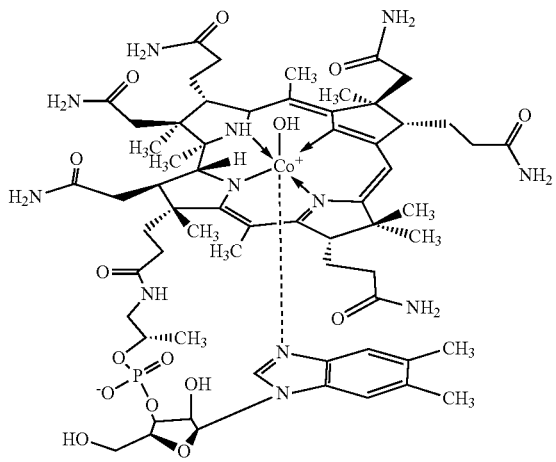

Formula I

Cyanokit (hydroxocobalamin for injection) 5 g for intravenous infusion is a cyanide antidote package which contains one colorless 250 mL glass vial, containing 5 g dark red lyophilized hydroxocobalamin, pH adjusted with hydrochloric acid, one transfer spike, one intravenous administration set, one quick use reference guide and one package insert.

The 5 g vial of hydroxocobalamin for injection is to be reconstituted with 200 mL of 0.9% NaCl, to give a dark red injectable solution (25 mg/mL). If 0.9% NaCl is not readily available, 200 mL of either Lactated Ringers injection or 5% Dextrose injection (D5W) may be used as the diluent. Diluent is not included in the Cyanokit. The pH of the reconstituted product ranges from 3.5 to 6.0. Hydroxocobalamin is a Dark red color crystalline powder. Hydroxocobalamin is freely soluble in water, methanol and dimethyl sulfoxide. Hydroxocobalamin is sparingly soluble in ethanol and is practically insoluble in ethyl acetate. Hydroxocobalamin is practically insoluble in acetone, ether, chloroform, and benzene. In aqueous buffers that span a pH range of 1.2 to 7.5, Hydroxocobalamin is highly soluble at pH 1.2 and 4.5, but shows low solubility (<0.4 mg/mL) at pH 6.8 and 7.5.

Hydroxocobalamin has been used for decades to treat acute cyanide poisoning in Europe and was approved for use in France in 1996. The simple mechanism of action is that hydroxocobalamin binds cyanide and forms nontoxic cyanocobalamin, which is excreted in urine. Hydroxocobalamin was recently approved in the United States for use as a component of the Cyanokit. Cyanokit (containing the drug hydroxocobalamin, intravenous tubing, and a sterile spike for reconstituting the drug product with saline) may be used in the United States and other countries for the treatment of known or suspected cyanide poisoning.

Cyanocobalamin is well known and constitutes vitamin B and has a CN group within an organic molecule of complex structure. For pharmaceutical use, there is today a tendency to prefer hydroxocobalamin, which frequently called vitamin B-12, to cyanocobalamin.

Hydroxocobalamin can be obtained by transferring CN group of cyanocobalamin to a hydroxyl group. This conversation helps hydroxocobalamin to enter more readily into the individual metabolism.

Various processes are already known for converting cyanocobalamin to hydroxocobalamin. For example, according to a known process, the CN-group is first eliminated in an acid medium from the cyanocobalamin molecule, and is replaced by another anion such as Cl", and then the resultant ester is converted to hydroxocobalamin.

However, some literature has suggested that this reaction has only a very low yield so that the process is without interest from the industrial aspect.

According to another known process, catalytic hydrogenation of the cyanocobalamin is carried out in order to convert it into cobalamin, which is then oxidised in order to give hydroxocobalamin.

U.S. Pat. No. 3,167,539, which is incorporated herein by reference, discusses the process for converting cyanocobalamin to hydroxocobalamin. The process includes reacting cyanocobalamin in aqueous media with a source of sulphite ions selected from the group consisting of a water soluble sulphite and sulphur dioxide to form Sulphitocobalamin, thereafter reacting Sulphitocobalamin with a source of nitrite ions selected from the group consisting of a water soluble nitrite and nitrous oxide to form Nitritocobalamin and then reacting Nitritocobalamin with a substance decomposing nitrous acid selected from the group consisting of urea and sulfamic acid to form hydroxocobalamin. PCT Pub. No. WO2014/142640, which is incorporated herein by reference, discusses a similar kind of process involving formation of cobalamin sulphite, Nitro cobalamin to get hydroxocobalamin.

The drawbacks of the above processes are more number of steps, which leads to a higher number of impurities, the use of an expensive catalyst and the fact that it is necessary to handle hydrogen gas, which is always dangerous. Furthermore, the reaction is not stoichiometric. Numerous factors come into play, particularly the efficacy of the catalyst, to modify the reducing power of the resultant hydrogen. The process may then result in very low yields owing to destruction of the cobalamin molecule if the reduction is carried too far.

Hydroxocobalamin can also be obtained by enzymatic process. Enzyme synthesis are described in GB Patent No. 1012360, U.S. Pat. Nos. 3,448,099 and 5,338,418, which are incorporated herein by reference. However, the process wherein hydroxocobalamin is obtained from coenzyme-type vitamin B12 is not advantageous with respect to yield, production costs, and the like. Such a process requires complex and numerous steps.

Another U.S. Pat. No. 3,138,583 discusses the process for preparation of hydroxocobalamin from cyanocobalamin using Zn granules & HCl to generate nascent hydrogen to reduce the cyanocobalamin to cobalamin then after oxygen purging product oxidized to hydroxocobalamin.

It has previously been proposed to convert cyanocobalamin to hydroxocobalamin by reduction, either by hydrogenation or by chemical reduction followed by re-oxidation, but such methods give rise to relatively poor yields being accompanied by undesirable degradation of the desired substance. It has also been proposed to affect the desired conversion by exposing cyanocobalamin to visible light under slightly acidic conditions accompanied by aeration. This conversion, however, is slow and unsuitable for application on the commercial scale. Undesirable degradation also tends to take place.

Drawbacks are observed by following a prior process such as high presence of cyanocobalamin and content of metal in hydroxocobalamin. Metal limits are not achieved by following a prior art process.

It is thus an object of at least one embodiment disclosed in the present application to provide an improved process for the conversion of cyanocobalamin to hydroxocobalamin which is convenient to use on the commercial scale and which is attended by less risk of degradation.

The present application therefore relates to preparation of hydroxocobalamin hydrochloride as well as their use in the treatment cyanide poisoning. The present application describes improved industrial robust scale process for the preparation of hydroxocobalamin hydrochloride of formula II with better yield and purity.

SUMMERY OF THE INVENTION

In general, the present application provides methods for synthesis of hydroxocobalamin hydrochloride of formula II.

The main object of at least one embodiment of the present application is to develop the improved process for the preparation of Hydroxocobalamin hydrochloride, which may include the steps of:

a) Reaction of cyanocobalamin of formula IV to get crude hydroxocobalamin of formula III.

b) Purification of crude hydroxocobalamin of formula III to afford pure hydroxocobalamin hydrochloride of formula II.

In a second embodiment, the present application relates to novel amorphous form and process for the preparation of same.

Schematic representation of improved process is depicted below:

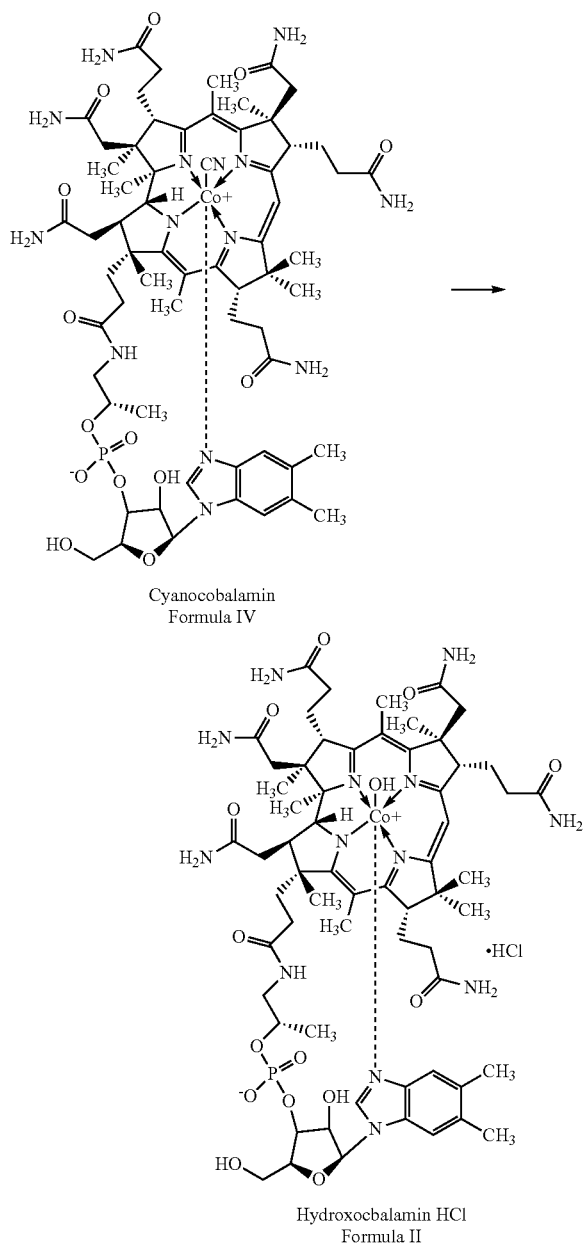

Cyanocobalamin
Formula IV

Hydroxocbalamin HCl
Formula II

DETAILED DESCRIPTION OF THE INVENTION

Figure 1:
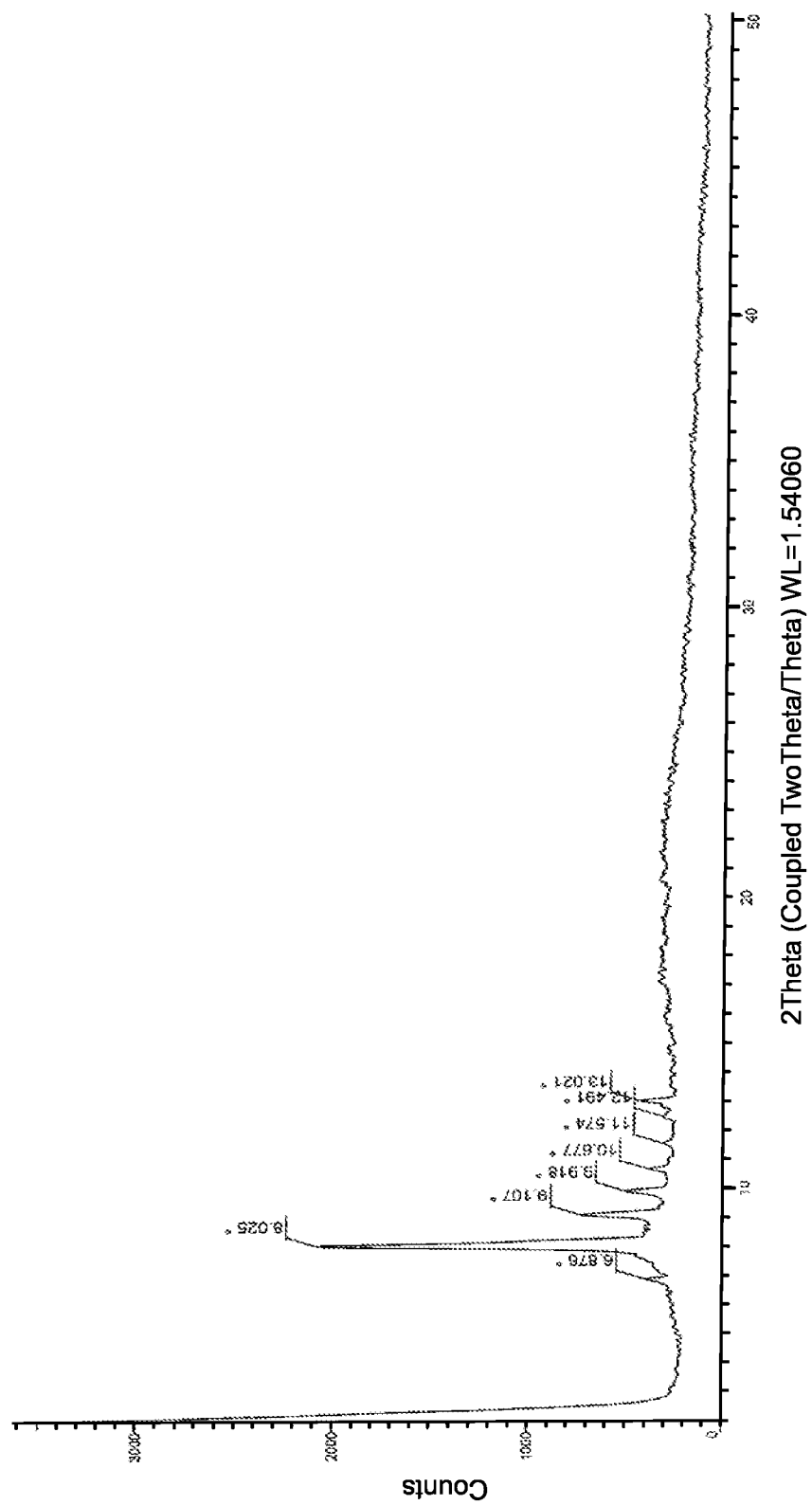
FIG. 1—illustrates a characteristic X-ray powder diffraction pattern of hydroxocobalamin hydrochloride.

Embodiments of the present invention now will be described more fully hereinafter with reference to the accompanying examples and experiments, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All percentages and ratios used herein are by weight of the total composition and all measurements made are at 25° C. and normal pressure unless otherwise designated. All temperatures are in degrees Celsius unless specified otherwise.

As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values.

Important aspects in the preparation of Hydroxocobalamin are quality and production costs of the end product. Owing to regulatory requirements, high quality standards have to be met. Of interest in this context are purity and content of the active compound. Coupled to purity, it is in particular the spectrum of by-products which needs to be monitored. Minor components have to be toxicologically qualified and assessed. Accordingly, they are listed in specifications and the maximum occurrence in the product is defined. For reasons of product safety and for the good of the patient, the by-product spectrum and the presence of individual contaminants are kept as low as possible to achieve the desire result.

In the first embodiment, the present invention involves improved process for the preparation of Hydroxocobalamin comprising the steps of
  a) Substitution reaction of cyanocobalamin of formula IV to get crude hydroxocobalamin of formula III.
  b) Purification of crude hydroxocobalamin of formula III to afford pure hydroxocobalamin hydrochloride of formula II.

A second embodiment of present invention relates to novel amorphous form and process for the preparation of same.

Schematic representation of improved process is depicted below:

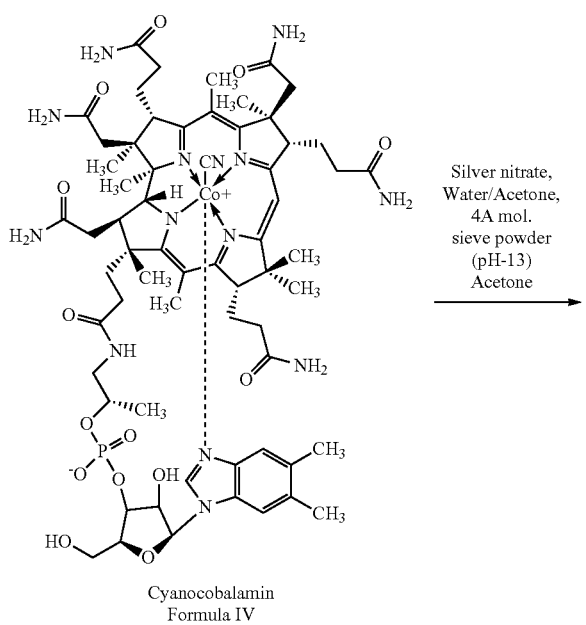

Cyanocobalamin
Formula IV

Silver nitrate,
Water/Acetone,
4A mol.
sieve powder
(pH-13)
Acetone

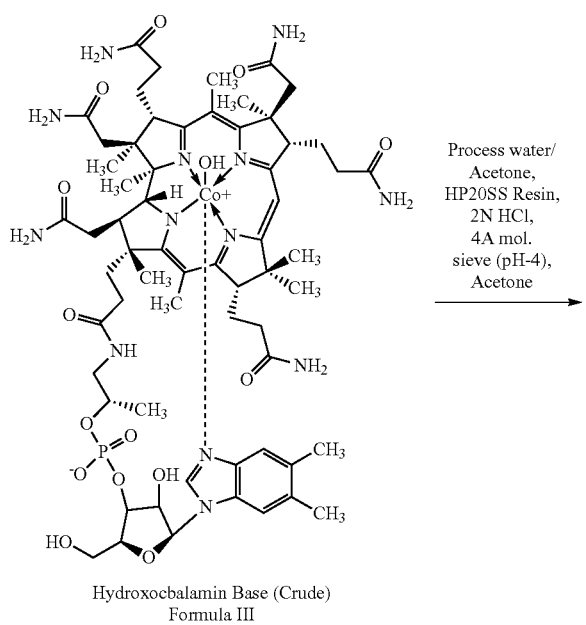

Hydroxocbalamin Base (Crude)
Formula III

Process water/
Acetone,
HP20SS Resin,
2N HCl,
4A mol.
sieve (pH-4),
Acetone

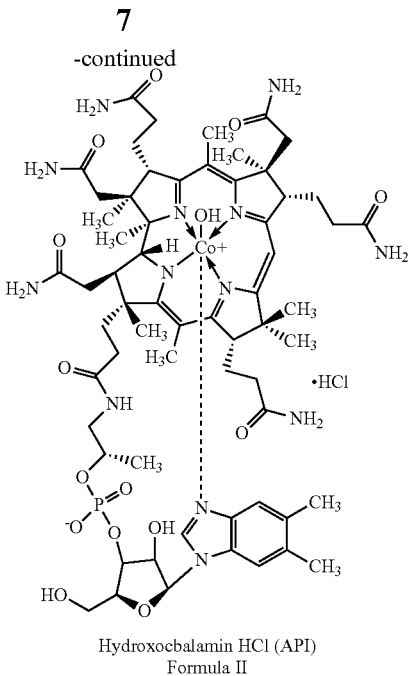

Hydroxocbalamin HCl (API)
Formula II

Substitution reaction in step a) includes; reaction of cyanocobalamin with silver nitrate by using water and methanol combination solvent system to get crude hydroxocobalamin.

Nitrate reagent required for the step a to proceed is not limited to silver nitrate sodium nitrate, potassium nitrate, lithium nitrate, rubidium nitrate, caesium nitrate, copper nitrate, cobalt nitrate, nickel nitrate, palladium nitrate etc.

Suitable solvents which can be used in step a for the preparation of compound II includes alcohols such as methanol, ethanol, isopropanol, butanol and the like; aqueous solvent like water; nitriles such as acetonitrile, propionitrile and the like; cyclic ether such as tetrahydrofuran, furan, ethylene oxide, solvents like DMSO, DMF, DMA and the like; any mixtures of two or more thereof. Preferably alcohol solvent, more preferably methanol.

A suitable temperature for the reaction of step a, may be from about 10° to about 40° C., preferably between 20° C. to 30° C., or any other suitable temperatures. The reaction may be carried out for any desired time period ranging from about 30 minutes to about 24 hours or longer.

The isolation of crude intermediate may be induced by using conventional techniques known in the art. For example, useful techniques include but are not limited to concentrating, cooling, separation, stirring, shaking, combining with an anti-solvent, adding seed crystals, evaporation, flash evaporation, simple evaporation, rotational drying, or the like. In particular crude product is obtained by adding the clear solution into anti solvent system to get isolated crude intermediate.

The resulting intermediate may be optionally further purified by using conventional technique known in the art. The techniques may include but not limited to treating the crude product into suitable solvent to get slurry. In particular purification involves a step b); dissolving crude hydroxocobalamin in suitable solvent to get clear solution. The clear solution is then treated with resin to remove un-reacted cyanocobalamin from previous stage. The pH of the clear solution may be adjusted with acid to afford pure hydroxocobalamin hydrochloride of formula II. By following the process it may content a high chloride content in such a case after adjusting a pH to acidic, base is added to increase the pH to lower acidic range like 3.5-4.5. Obtained hydroxocobalamin HCl then optionally may be further treated with alcoholic solvent to get an amorphous form.

The pH may be adjusted with acid selected from Hydrochloric Acid, H2SO4, nitric acid, carbonic acid, hydrofluoric acid. Phosphoric acid.

The pH may be adjusted with base selected from Sodium Hydroxide, calcium hydroxide, barium hydroxide, potassium hydroxide, strontium hydroxide, aluminium hydroxide, magnesium hydroxide, ammonia.

Suitable solvent in step b) is selected from water, methanol, acetonitrile, IPA, THF, Ethyl acetate, Dioxane, Toluene and dichloromethane In particular, water is preferably selected for dissolving crude product. Resin may then be added in above solution and filtered to remove un-reacted cyanocobalamin. Resin may be selected from Diaion HP20SS, Diaion HP20, Dowex 50w, Amberlite IRA 402 (Cl), Amberlite IRA402(OH), Sephabed SP700, Amberlite IRA67 Base, DEAE sephadex, Amberlite IR 120H/Na+ and the like. Preferably, Diaion HP20SS is selected. pH of the clear solution may then be adjusted with 2.0-4.0 by using hydrochloric acid. Pure hydroxocobalamin may then isolated by using acetone as anti-solvent. Alcoholic solvent to get amorphous form may be selected from methanol or ethanol. In a particular case, methanol is selected.

The Isolation of pure intermediate can be done by decantation, centrifugation, gravity filtration, suction filtration and like. Drying can be carried out in a tray dryer, vacuum oven, air oven, cone vacuum dryer, rotary vacuum dryer, fluidized bed dryer, spin flash dryer, flash dryer, or the like. The drying can be carried out less than about 60° C., less than about 40° C., less than about 30° C., less than about 20° C., or any other suitable temperatures; at atmospheric pressure or under a reduced pressure; as long as the crystalline intermediate is not degraded in its quality. The drying can be carried out for any desired times until the required product quality is achieved. In a particular embodiment, drying is done at 25-35° C. Suitable time for drying can vary from few minutes to several hours for example from about 30 minutes to about 24 or more hours.

The Hydroxocobalamin hydrochloride synthesize by this route have advantageous as the reported process having the use of multistep synthesis with huge volume of solvent & reagents, use of phenol-chloroform for product isolation & leads to lot of process impurities. Another reported process using zinc metals also does not meet the purity specification and also hydrogen gas will be generated during process which is not recommended safety point of view, current application provides the better control for impurities with avoiding tedious work up process and less use of multiple reagents & isolation also only in simple solvents like Acetone. Product obtained by this route have advantageous properties selected from at least one of: chemical purity, stability—such as storage stability, stability to dehydration, stability to polymorphic conversion, flowability, solubility, morphology or crystal habit, low hygroscopicity and low content of residual solvents.

Hydroxocobalamin HCl obtained through below mentioned process is either an amorphous or crystalline in nature. Form is characterised through various techniques such as XRD, DSC and TGA.

Certain specific aspects and embodiments of the present application will be explained in more detail with reference to the following examples, which are provided only for purposes of illustration and should not be construed as limiting the scope of the present application in any manner.

EXPERIMENTAL SECTION

Preparation of Crystalline Hydroxocobalamin (Step B)

Process A: Crude material dissolve in water & then charge resin (HP20SS), stir for 1.0 hr. Filter the solid resin. Filtrate pH adjust to 2.0-4.0 by using 2N HCl, charge Zeolite stir it & then filter, charge acetone to get complete material precipitation. Dark red crystalline powder obtains. Yield range—0.5-0.8 w/w.

Process B: Crude material dissolve in water & then charge resin (HP20SS), stir for 1.0 hr. Filter the solid resin. Filtrate pH adjust to 2.0-2.2 using 2N HCl, after maintaining the reaction mass pH adjusted to 3.8-4.2 using 0.1 N NaOH solution. After maintaining reaction mass filtered through 0.45-micron paper then charge acetone to get complete material precipitation. Dark red crystalline powder obtains.

Yield range—0.5-0.8 w/w.

Chloride content 2.4-2.7, pH—4.5-5.5 & Silver NMT 1.0 ppm.

Figure 2:
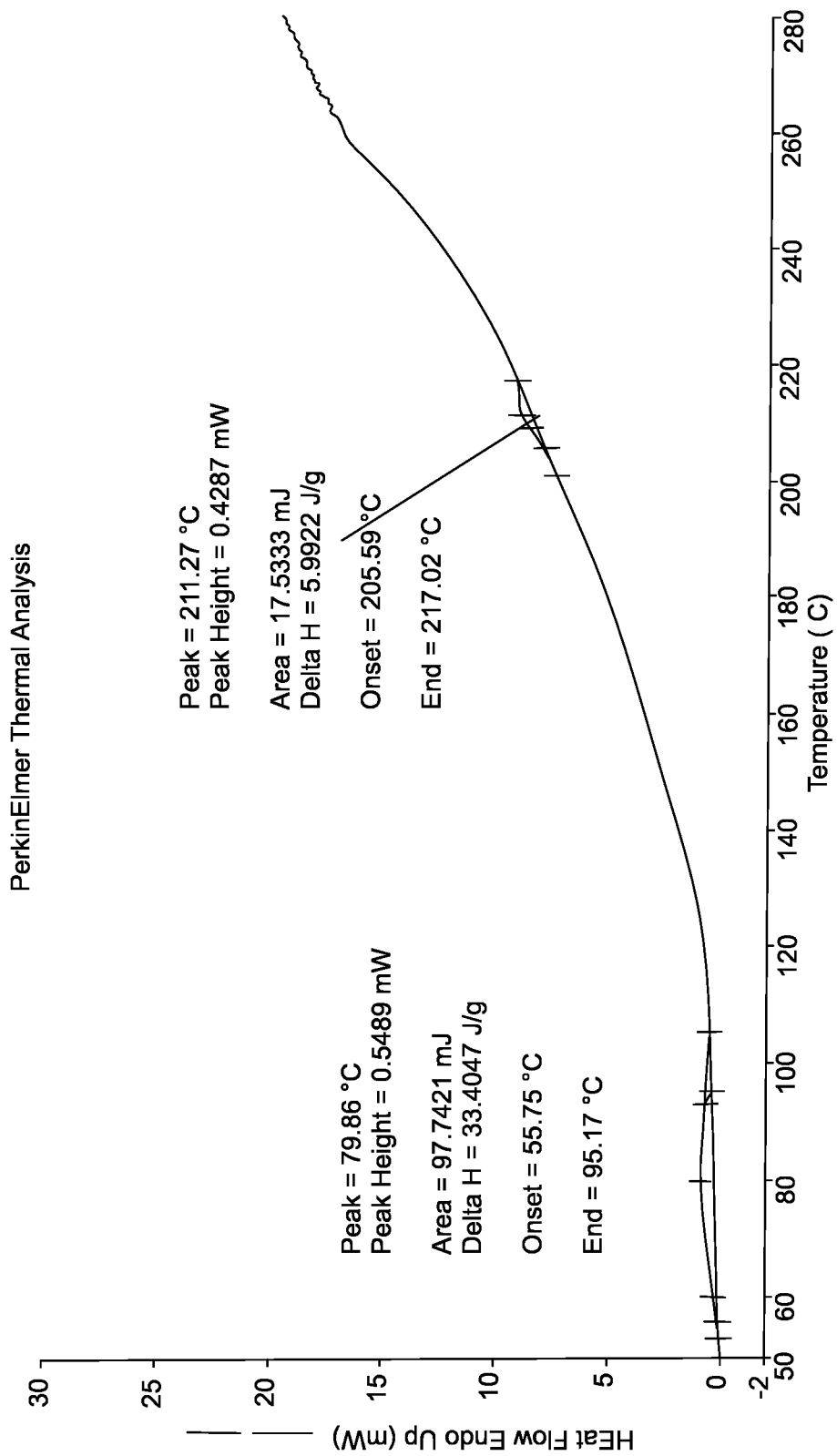
FIG. 2—illustrates a characteristic DSC pattern of hydroxocobalamin hydrochloride.
Figure 3:
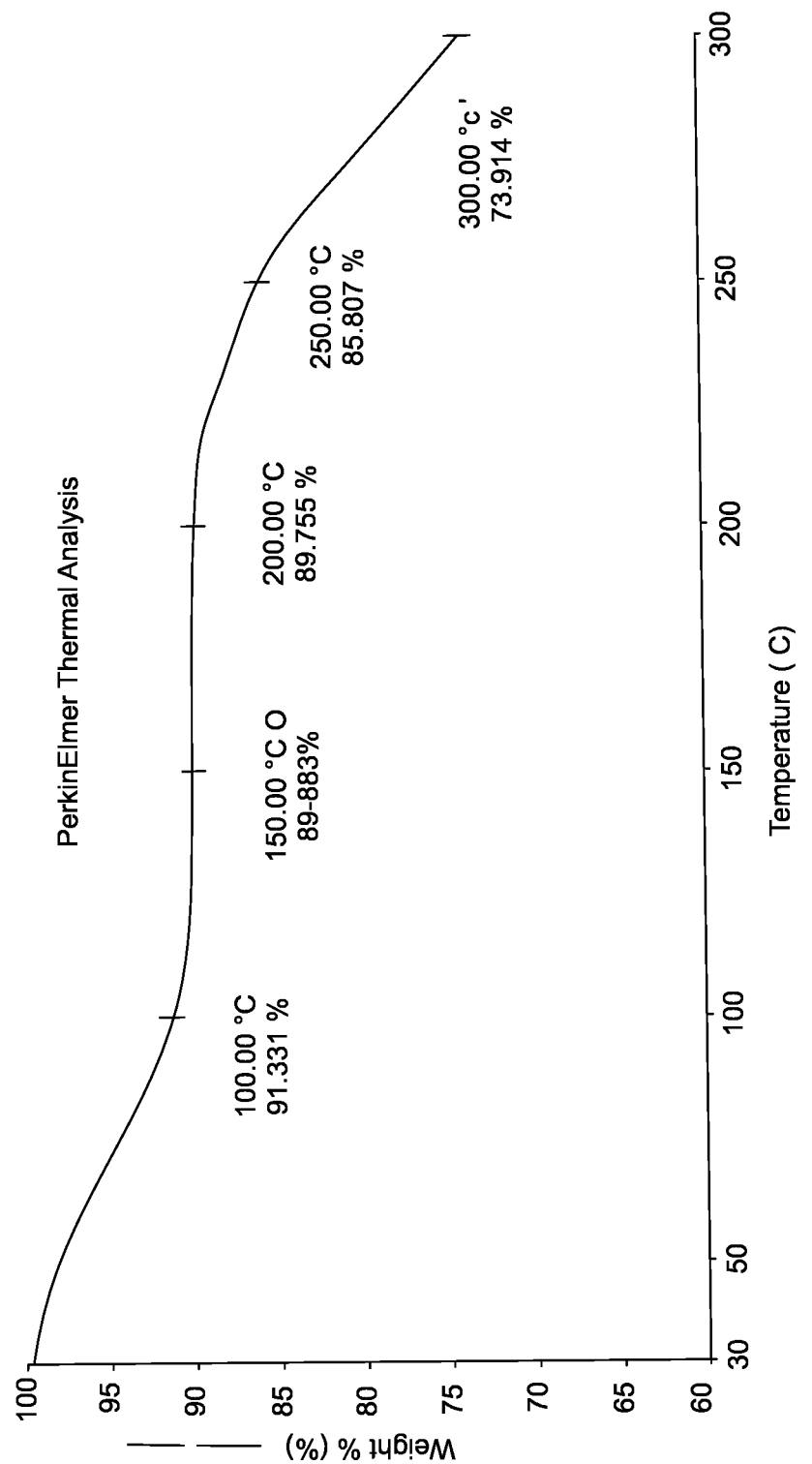
FIG. 3—illustrates a characteristic TGA pattern of hydroxocobalamin hydrochloride.

Hydroxocobalamin obtained through this process is crystalline in nature, confirmed by XRD and has DSC peak at 79.860C and 211.270C. Results of this characterisation with XRD, DSC and TGA data is illustrated in respective drawing FIG. 1, FIG. 2 and FIG. 3.

Preparation of Amorphous Hydroxocobalamin (Step B)

Crude material dissolve in water & then charge resin (HP20SS), stir for 1.0 hr. Filter the solid resin. Filtrate pH adjust to 2.0-2.2 using 2N HCl, after maintaining the reaction mass filtered through 0.45-micron paper then charge acetone to get complete material precipitation. Yield range—0.5-0.8 w/w.

Dissolve the above solid in Methanol (125 ml) to get clear solution then charge Zeolite (pH 4) and stir reaction mass for 1.0 hr. Filter the resin & filtrate charge to Acetone to get solid Orange-Red amorphous solid obtains.

Yield range—0.5-0.6 w/w.

Figure 4:
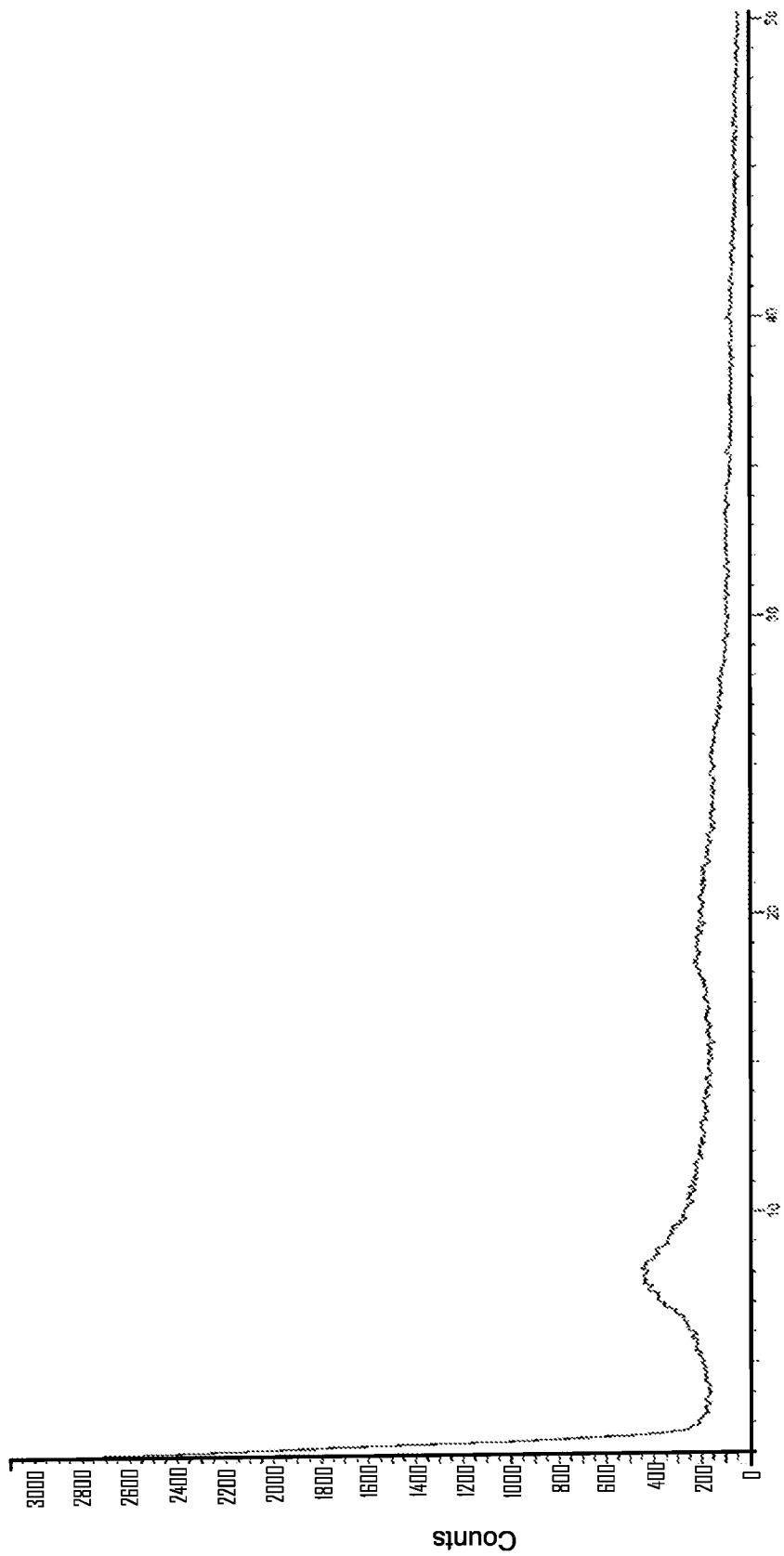
FIG. 4—illustrates a characteristic X-ray powder diffraction pattern of amorphous hydroxocobalamin hydrochloride.
Figure 5:
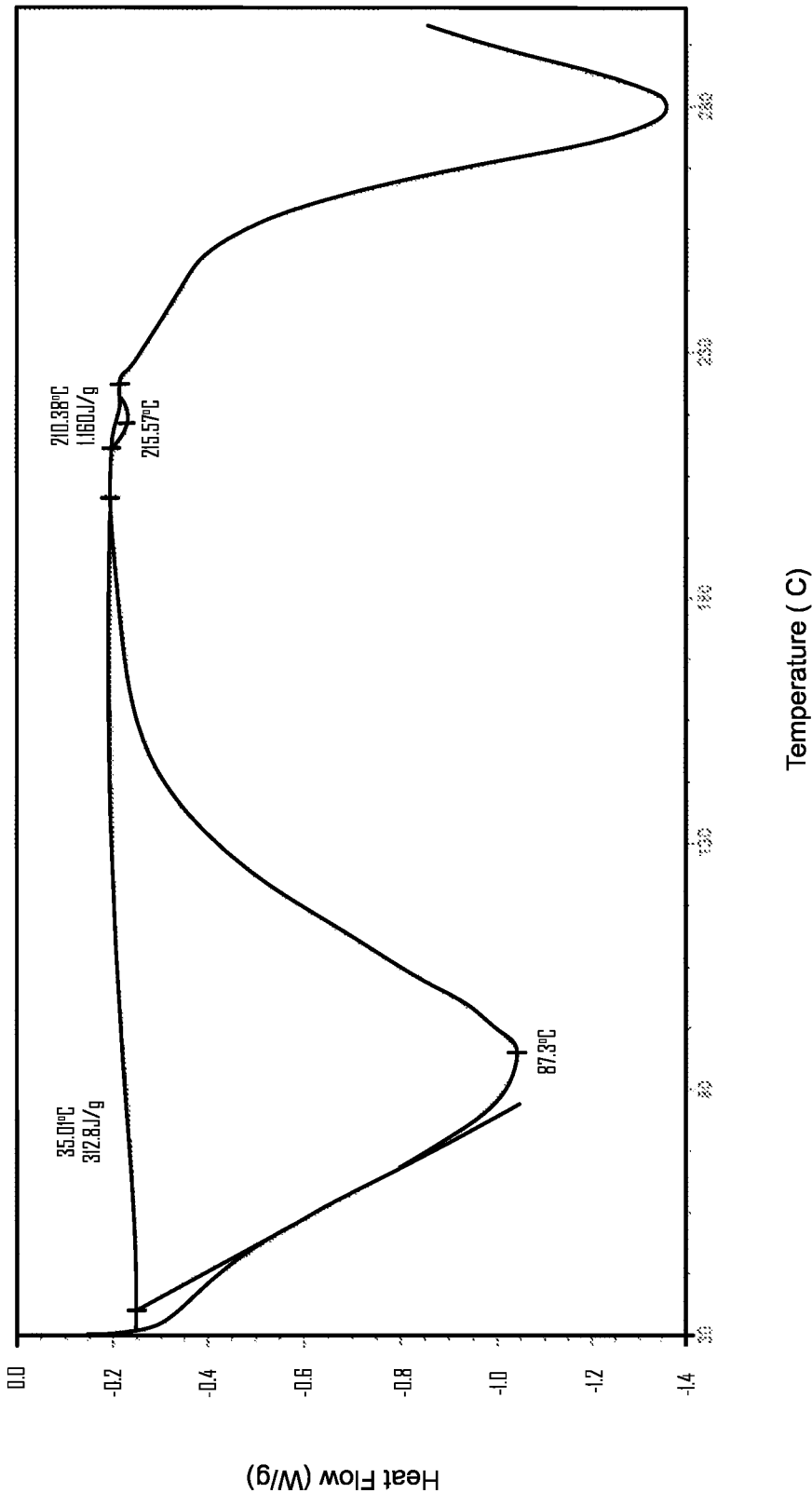
FIG. 5—illustrates a characteristic DSC pattern of amorphous hydroxocobalamin hydrochloride.
Figure 6:
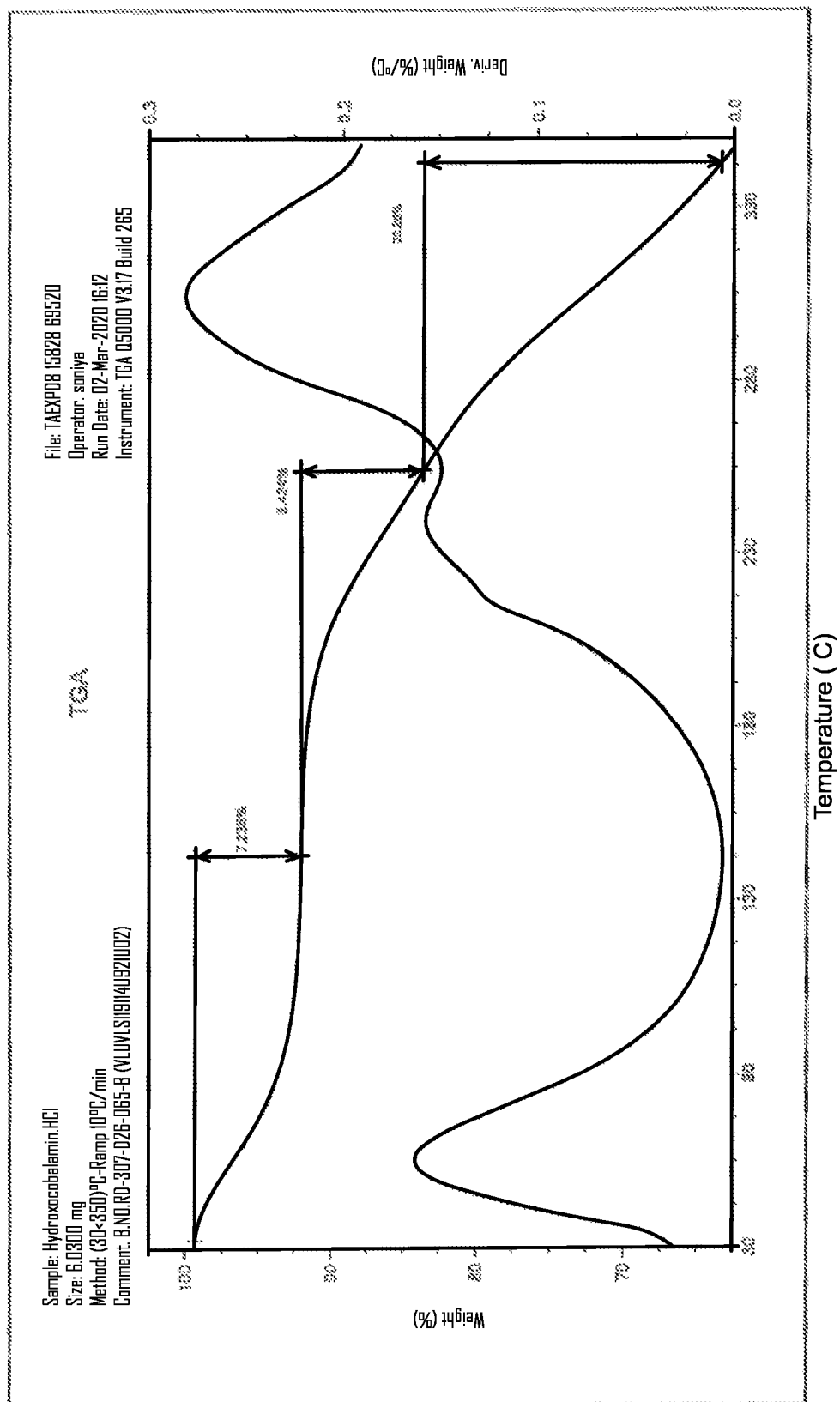
FIG. 6—illustrates a characteristic TGA pattern of amorphous hydroxocobalamin hydrochloride.

Hydroxocobalamin obtained through this process is amorphous in nature, confirmed by XRD and has DSC peak at 87.31° C. & 215.57° C. and TGA data. Results of this characterisation with XRD, DSC and TGA data is illustrated in respective drawing FIG. 4, FIG. 5 and FIG. 6.

We claim:

1. A process for the purification of Hydroxocobalamin, comprising the steps of:
    a. dissolving a crude hydroxocobalamin in solvent to a clear solution, wherein the crude hydroxocobalamin comprises un-reacted cyanocobalamin resulting from a formation of the crude hydroxocobalamin using a nitrate reagent and wherein the solution is prepared without using phenol chloroform;
    b. treating the clear solution with resin to remove the un-reacted cyanocobalamin from the crude hydroxocobalamin;
    c. filtering the treated solution to remove solid resin therefrom and using an acid adjusting the filtrate pH to 2.0-2.2;
    d. re-adjusting pH using a base to 3.8-4.5 to reduce chloride content; and
    e. adding anti-solvent to precipitate there from pure hydroxocobalamin.

2. The process for the purification of Hydroxocobalamin as claimed in claim 1, wherein the resin is at least one of: Diaion HP20SS, Diaion HP20, Dowex 50w, Amberlite IRA 402(Cl), Amberlite IRA402(OH), Sephabed SP700, Amberlite IRA67 Base, DEAE sephadex, or Amberlite IR 120H/Na+.

3. The process for the purification of Hydroxocobalamin as claimed in claim 1, wherein pH is adjusted with the acid selected from at least one of Hydrochloric Acid, H2SO4, nitric acid, carbonic acid, hydrofluoric acid, or Phosphoric acid.

4. The process for the purification of Hydroxocobalamin as claimed in claim 1 wherein pH is re-adjusted with the base selected from at least one of Sodium Hydroxide, calcium hydroxide, barium hydroxide, potassium hydroxide, strontium hydroxide, aluminium hydroxide, magnesium hydroxide, or ammonia.

5. The process for the purification of Hydroxocobalamin as claimed in claim 1 comprising treating the pure hydroxocobalamin precipitate with an alcoholic solvent to yield hydroxocobalamin in amorphous form.

6. The process for the purification of Hydroxocobalamin as claimed in claim 1 comprising precipitating Hydroxocobalamin from the solution completely.

* * * * *